(12) United States Patent
Mitchell et al.

(10) Patent No.: US 9,442,362 B2
(45) Date of Patent: Sep. 13, 2016

(54) METHOD AND APPARATUS FOR GENERATING THREE-DIMENSIONAL IMAGE INFORMATION

(75) Inventors: Thomas N. Mitchell, Bowen Island (CA); Ichiro Shinkoda, Vancouver (CA)

(73) Assignee: Steropes Technologies, LLC, Gulf Breeze, FL (US)

( * ) Notice: Subject to any disclaimer, the term of this patent is extended or adjusted under 35 U.S.C. 154(b) by 1146 days.

(21) Appl. No.: 13/382,892

(22) PCT Filed: Jul. 12, 2010

(86) PCT No.: PCT/CA2010/001093
§ 371 (c)(1),
(2), (4) Date: Mar. 16, 2012

(87) PCT Pub. No.: WO2011/003208
PCT Pub. Date: Jan. 13, 2011

(65) Prior Publication Data
US 2013/0038690 A1     Feb. 14, 2013

(30) Foreign Application Priority Data

Jul. 10, 2009   (WO) ................ PCT/CA2009/000957

(51) Int. Cl.
*H04N 5/232*      (2006.01)
*G03B 35/04*     (2006.01)
(Continued)

(52) U.S. Cl.
CPC ........... *G03B 35/04* (2013.01); *A61B 1/00193* (2013.01); *A61B 1/04* (2013.01); *G03B 35/02* (2013.01); *H04N 13/021* (2013.01); *H04N 13/0217* (2013.01)

(58) Field of Classification Search
CPC .................. H04N 15/00; G06T 19/20; G06T 2207/10004; G06T 3/40; G06T 7/0051; G06F 3/013
See application file for complete search history.

(56) References Cited

U.S. PATENT DOCUMENTS

| 2,255,631 A | 9/1941 | Schulman |
| 3,464,766 A | 9/1969 | Knauf |

(Continued)

FOREIGN PATENT DOCUMENTS

| CA | 2177165 A1 | 6/1995 |
| CA | 2457506 A1 | 3/2003 |

(Continued)

OTHER PUBLICATIONS

Anonymous. (Jun. 1993)."3-D Imaging for Minimally Invasive Surgery gets MDs' Attention," *Health Technology Trends* 5(6):4-5.

(Continued)

*Primary Examiner* — Chikaodili E Anyikire
*Assistant Examiner* — Kehinde O Abimbola
(74) *Attorney, Agent, or Firm* — Morrison & Foerster LLP

(57) ABSTRACT

A method and apparatus involves directing light captured within the field of view of the lens to an aperture plane of the lens, receiving the captured light at a spatial discriminator located proximate the aperture plane, the discriminator including a first portion disposed to transmit light having a first optical state through a first portion of the single imaging path and a second portion disposed to transmit light having a second optical state through a second portion of the single imaging path. The first and second portions of the single imaging path provide respective first and second perspective viewpoints within the field of view of the lens for forming respective first and second images at an image sensor disposed at an image plane of the lens. The first and second images together being operable to represent three dimensional spatial attributes of the objects.

25 Claims, 5 Drawing Sheets

(51) Int. Cl.
   *A61B 1/00* (2006.01)
   *A61B 1/04* (2006.01)
   *H04N 13/02* (2006.01)
   *G03B 35/02* (2006.01)

(56) References Cited

U.S. PATENT DOCUMENTS

| | | | |
|---|---|---|---|
| 3,712,199 A | 1/1973 | Songer, Jr. | |
| 3,784,291 A | 1/1974 | Hirata et al. | |
| 4,021,846 A | 5/1977 | Roese | |
| 4,059,336 A | 11/1977 | Hopkins | |
| 4,103,260 A * | 7/1978 | Buchman | G02F 1/01 359/250 |
| 4,196,966 A | 4/1980 | Malis | |
| 4,303,316 A | 12/1981 | McElveen | |
| 4,392,710 A | 7/1983 | Rogers | |
| 4,568,160 A | 2/1986 | Krueger | |
| 4,601,552 A | 7/1986 | Jessmore | |
| 4,651,201 A | 3/1987 | Schoolman | |
| 4,761,066 A | 8/1988 | Carter | |
| 4,924,853 A | 5/1990 | Jones, Jr. et al. | |
| 5,059,009 A | 10/1991 | McKinley | |
| 5,094,523 A | 3/1992 | Reznichenko et al. | |
| 5,097,359 A | 3/1992 | McKinley | |
| 5,122,650 A | 6/1992 | McKinley | |
| 5,222,477 A | 6/1993 | Lia | |
| 5,471,237 A | 11/1995 | Shipp | |
| 5,532,777 A | 7/1996 | Zanen | |
| 5,588,948 A | 12/1996 | Takahashi et al. | |
| 5,671,450 A | 9/1997 | Suzuki | |
| 5,703,677 A | 12/1997 | Simoncelli et al. | |
| 5,720,706 A | 2/1998 | Takahashi | |
| RE35,816 E | 6/1998 | Schulz | |
| 5,828,487 A | 10/1998 | Greening et al. | |
| 5,835,133 A | 11/1998 | Moreton et al. | |
| 6,006,001 A | 12/1999 | Alfano et al. | |
| 6,151,164 A | 11/2000 | Greening et al. | |
| 6,275,335 B1 | 8/2001 | Costales | |
| 6,348,994 B1 | 2/2002 | Geier et al. | |
| 6,359,664 B1 | 3/2002 | Faris | |
| 6,400,394 B1 | 6/2002 | Kim et al. | |
| 6,546,208 B1 | 4/2003 | Costales | |
| 6,624,935 B2 | 9/2003 | Weissman et al. | |
| 6,683,716 B1 | 1/2004 | Costales | |
| 7,324,279 B2 | 1/2008 | Penn | |
| 7,683,926 B2 | 3/2010 | Schechterman et al. | |
| 7,978,892 B2 | 7/2011 | Quadling et al. | |
| 2002/0131170 A1 | 9/2002 | Costales | |
| 2006/0132794 A1 * | 6/2006 | Badami | G01B 11/161 356/492 |
| 2006/0279740 A1 * | 12/2006 | Badami | G01B 9/02028 356/485 |
| 2007/0132953 A1 | 6/2007 | Silverstein | |
| 2007/0188863 A1 | 8/2007 | Sun et al. | |
| 2008/0239135 A1 | 10/2008 | Tamura | |
| 2009/0116729 A1 * | 5/2009 | Cheng | G01D 5/58 382/154 |
| 2009/0119061 A1 * | 5/2009 | Cheng | G01B 11/2545 702/151 |
| 2009/0207379 A1 * | 8/2009 | Oakley | G02B 27/283 353/20 |
| 2009/0279784 A1 * | 11/2009 | Arcas | G06T 17/00 382/190 |
| 2009/0310851 A1 * | 12/2009 | Arcas | G06T 7/0065 382/154 |
| 2010/0103276 A1 * | 4/2010 | Border | H04N 13/0207 348/222.1 |
| 2012/0188347 A1 | 7/2012 | Mitchell et al. | |

FOREIGN PATENT DOCUMENTS

| | | |
|---|---|---|
| CA | 2545418 A1 | 5/2005 |
| WO | WO-95/14952 A1 | 6/1995 |
| WO | WO-97/03378 A1 | 1/1997 |
| WO | WO-01/91472 A2 | 11/2001 |
| WO | WO-01/91472 A3 | 11/2001 |

OTHER PUBLICATIONS

Chinese Office Action mailed on Dec. 25, 2013, for Chinese Patent Application No. 201080040644.3, 30 pages. (with English translation).

International Search Report mailed on Sep. 21, 2010, for PCT Patent Application No. PCT/CA2010/001093, filed on Jul. 12, 2010, 10 pages.

International Search Report mailed on Mar. 18, 2010, for PCT Patent Application No. PCT/CA2009/000957, filed on Jul. 10, 2009, 7 pages.

Mitchell, T.N. et al. (Oct. 1993). "Three-Dimensional Endoscopic Imaging for Minimal Access Surgery," *JR Coll Surg Edinb* 38(5): 285-292.

Nagy, A.G. et al. (1993). "The Future: Telepresence and Other Developments Minimally Invasive Surgery in Gastro-Intestinal Cancer" Chapter 12 in *Minimally Invasive Surgery in Gastrointestinal Cancer*, published by Churchill Livingstone, pp. 171-184.

Nagy, A.G. et al. (Mar. 1994). "New Technologies in Laparoscopic Surgery," *BC Medical Journal* 36(3):179-183.

Written Opinion mailed on Sep. 21, 2010, for PCT Patent Application No. PCT/CA2010/001093, filed on Jul. 12, 2010, 5 pages.

Written Opinion mailed on Mar. 18, 2010, for PCT Patent Application No. PCT/CA2009/000957, filed on Jul. 10, 2009, 4 pages.

* cited by examiner

METHOD AND APPARATUS FOR GENERATING THREE-DIMENSIONAL IMAGE INFORMATION

CROSS REFERENCE TO RELATED APPLICATIONS

This application is a National Phase filing under 35 U.S.C. §371 of International Application PCT/CA2010/001093, with an International Filing Date of Jul. 12, 2010, entitled "METHOD AND APPARATUS FOR GENERATING THREE-DIMENSIONAL IMAGE INFORMATION, which claims the benefit of priority from PCT/CA2010/000957, with the priority filing date of Jul. 10, 2009 entitled "METHOD AND APARATUS FOR GENERATING THREE DIMENSIONAL IMAGE INFORMATION USING A SINGLE IMAGING PATH", which are hereby incorporated by reference in their entirety and for all purposes as if put forth in full below.;

BACKGROUND OF THE INVENTION

1. Field of Invention

This invention relates generally to generating three dimensional image information and more particularly to generating three dimensional image information using a single imaging path.

2. Description of Related Art

In conventional two-dimensional (2D) imaging, rays of light representing objects in a three-dimensional (3D) scene are captured and mapped onto a 2D image plane, and thus depth information is not recorded. Stereoscopic optical systems are capable of producing images that represent depth information by producing separate images from differing perspective viewpoints. The depth information may be used to produce 3D measurements between points in the scene, for example. Alternatively, the separate images may be separately presented to respective left and right eyes of a user so as to mimic operation of the human eyes in viewing a real scene and allowing the user to perceive depth in the presented views. The separated or stereo images are generally produced by an optical system having either a pair of spatially separated imaging paths or by using different portions of a single imaging path to produce images having differing perspective viewpoints. The images may then be presented using eyewear that is able to selectively permit the separate images to reach the user's respective left and right eyes. Alternatively, a special display may be configured to project spatially separated images toward the user's respective left and right eyes.

The use of stereoscopic imaging also finds application in the field of surgery where a 3D endoscope may be used to provide a 3D view to the surgeon. Stereoscopic imaging may also be useful in remote operations, such as undersea exploration for example, where control of a robotic actuator is facilitated by providing 3D image information to an operator who is located remotely from the actuator. Other applications of stereoscopic imaging may be found in physical measurement systems and in 3D film production equipment used in the entertainment industry.

SUMMARY OF THE INVENTION

In accordance with one aspect of the invention there is provided a method for generating three-dimensional image information using a lens having a single imaging path and an associated field of view. The method involves directing light captured within the field of view of the lens to an aperture plane of the lens, receiving the captured light at a spatial discriminator located proximate the aperture plane, the discriminator including a first portion disposed to transmit light having a first optical state through a first portion of the single imaging path and a second portion disposed to transmit light having a second optical state through a second portion of the single imaging path. The first and second portions of the single imaging path provide respective first and second perspective viewpoints within the field of view of the lens for forming respective first and second images at an image sensor disposed at an image plane of the lens. The first image represents objects within the field of view from the first perspective viewpoint and the second image represents the objects from the second perspective viewpoint, the first and second images together being operable to represent three dimensional spatial attributes of the objects. The method also involves receiving the first image at a first plurality of sensor elements on the image sensor, the first plurality of elements being responsive to light having the first optical state, and receiving the second image at a second plurality of sensor elements on the image sensor, the second plurality of elements being responsive to light having the second optical state.

Receiving the first and second images may involve receiving the first and second images at respective first and second pluralities of sensor elements each including a selective element operable to transmit light having a corresponding optical state and to block transmission of light having other than the corresponding optical state, and a corresponding sensor element underlying the selective element.

Each corresponding sensor element may include a plurality of sensor elements.

Receiving the first and second images may involve receiving the first and second images at respective first and second pluralities of sensor elements arranged in a repeating mosaic pattern operable to reduce spatial interference due to a repetition frequency of the sensor elements of the image sensor.

The first portion of the discriminator may include a first polarizer portion disposed to transmit light having a first polarization state through the first portion of the single imaging path and the second portion of the discriminator may include a second polarizer portion disposed to transmit light having a second polarization state through the second portion of the single imaging path.

Receiving the first image may involve receiving the first image at a first plurality of polarizer elements disposed to transmit light having the first polarization state to a corresponding plurality of sensor elements and to block transmission of light having the second polarization state, and receiving the second image may involve receiving the second image at a second plurality of polarizer elements disposed to transmit light having the second polarization state to a corresponding plurality of sensor elements and to block transmission of light having the first polarization state.

Receiving the captured light may involve receiving light having a left-handed elliptical polarization state through the first portion of the polarizer and receiving light having a right-handed elliptical polarization state through the second portion of the polarizer and receiving the first image may involve receiving the first image at a first plurality of polarizer elements operable to transmit light having a left-handed elliptical polarization state and to block light having a right-handed elliptical polarization state, and receiving the second image may involve receiving the second image at a second plurality of polarizer elements operable to transmit light having a right-handed elliptical polarization state and to block light having a left-handed elliptical polarization state.

Receiving the first image at the first plurality of polarizer elements may involve receiving the first image at a plurality of quarter wave plates operable to change the right-handed elliptical polarization state to a first linear polarization state and may further involve receiving the first image at a corresponding plurality linear polarizing elements operable to transmit light having the first linear polarization state, and receiving the second image at the second plurality of polarizer elements may involve receiving the second image at a plurality of quarter wave plates operable to change the left-handed elliptical polarization state to a second linear polarization state and may further involve receiving the second image at a corresponding plurality linear polarizing elements operable to transmit light having the second linear polarization state.

The left-handed elliptical polarization state may include a left-handed circular polarization state and the right-handed elliptical polarization state may include a right-handed circular polarization state.

Receiving the captured light may involve receiving light having a first linear polarization orientation through the first portion of the polarizer and receiving light having a second linear polarization orientation through the second portion of the polarizer, the first linear polarization orientation being oriented orthogonal to the second linear polarization orientation and receiving the first image at the first plurality of polarizer elements may involve receiving the first image at a plurality of polarizer elements operable to transmit light having a first linear polarization state and to block light having a right-handed elliptical polarization state, and receiving the second image at the second plurality of polarizer elements may involve receiving the second image at a plurality of polarizer elements operable to transmit light having a second linear polarization state and to block light having a left-handed elliptical polarization state.

The first linear polarization orientation may be oriented at 45 degrees.

Receiving the first image at the first plurality of polarizer elements may involve receiving the first image at a plurality of linear polarizer elements operable to transmit light having the first polarization state, and receiving the second image at the second plurality of polarizer elements may involve receiving the second image at a plurality of linear polarizer elements operable to transmit light having the second polarization state.

The method may involve selectively rotating the discriminator by about 90 degrees to generate images in one of a landscape orientation and a portrait orientation.

The first portion of the discriminator may include a first filter portion disposed to transmit light having first spectral attributes through the first portion of the single imaging path and the second portion of the discriminator may include a second discriminator portion disposed to transmit light having second spectral attributes through a second portion of the single imaging path, and receiving the first image may involve receiving the first image at a first plurality of sensor elements operable to transmit light having the first spectral attributes and to block transmission of light having the second spectral attributes, and receiving the second image may involve receiving the second image at a second plurality of sensor elements operable to transmit light having the second spectral attributes and to block transmission of light having the first spectral attributes.

The first spectral attributes may include a first set of wavelengths and the second spectral attributes may include a second set of wavelengths, the first and second sets of wavelengths being separated in wavelength by a wavelength difference.

Each sensor element may include a plurality of filter elements, each filter element being operable to transmit light in a wavelength range within the set of wavelength ranges.

The plurality of filter elements may be disposed such that light passing through the sensor element passes successively through each of the filter elements before reaching an underlying color filter array.

The plurality of filter elements may be disposed adjacent to each other and overlying corresponding sensor elements and the filter elements are configured to simultaneously generate the first and second images while directing light to corresponding underlying sensor elements for generating color information.

The method may involve generating an image signal representing the first and second images, and may further involve and processing the imaging signal to generate a first imaging signal representing the first image received by the first plurality of sensor elements and to generate a second imaging signal representing the second image received by the second plurality of sensor elements, and the processing may include image processing of the first and second image signals to cause the first and second images to have the same color appearance.

Each of the first and second sets of wavelengths may include red, green, and blue wavelengths and the wavelength difference may be between about 1 nanometer and about 100 nanometers.

Receiving the first image may involve receiving the first image at a first plurality of sensor elements having an overlying filter element operable to transmit light having the first spectral attributes and receiving the second image at a second plurality of sensor elements having an overlying filter element operable to transmit light having the second spectral attributes.

The filter elements each may include a narrow optical band pass filter having a spectral response corresponding to the respective first and second spectral attributes.

The first portion of the discriminator may include a filter element operable to transmit the first set of wavelengths of light and the second portion of the discriminator may include a filter element operable to transmit the second set of wavelengths of light.

The method may involve generating an image signal representing the first and second images.

Generating the imaging signal may involve causing the image sensor to generate a first imaging signal representing the first image received by the first plurality of sensor elements and causing the image sensor to generate a second imaging signal representing the second image received by the second plurality of sensor elements.

Generating the imaging signal may involve causing the image sensor to generate an imaging signal representing light received at each of the first and second pluralities of sensor elements, and may further involve processing the imaging signal to generate a first imaging signal representing the first image received by the first plurality of sensor elements and to generate a second imaging signal representing the second image received by the second plurality of sensor elements.

Directing light to an aperture plane of the lens may involve directing light captured within the field of view of the lens to an aperture plane of the lens located at one of a location of a physical aperture of the lens, or a location of a conjugate of the physical aperture.

Receiving the captured light at the discriminator may involve receiving the captured light at a discriminator displaced from the aperture plane by a sufficiently small displacement such that intensity variations in the first and second images due to vignetting by the first and second portion of the discriminator may be below a threshold that may be detectable by the human eye.

The displacement may be sufficiently small to reduce the intensity variations to below 30% across an image plane associated with the first and second images.

Receiving the captured light at the discriminator may involve receiving captured light at a discriminator coating applied to a surface of a lens element disposed proximate to the aperture plane.

The lens may include a plurality of generally circular lens elements defining a generally circular cross-section single imaging path and receiving the captured light may involve transmitting light having the first optical state through a left half of the discriminator and transmitting the light having the second optical state through a right half of the discriminator, the respective left and right halves of the discriminator defining respective left and right semicircular portions of the single imaging path.

The lens may include a plurality of generally circular lens elements defining a generally circular cross-section single imaging path and receiving the captured light may involve transmitting light having the first optical state through a left sector portion of the discriminator and transmitting the light having the second optical state through a right sector portion of the discriminator, the left and right sector portions being disposed about a vertical centerline of the lens.

The method may involve varying an extent of the first and second portions of the imaging path to cause the first and second perspective viewpoints to change location while forming the first and second images, the change in perspective viewpoint location providing a corresponding change in the representation of the three dimensional spatial attributes.

The lens may include a first aperture disposed to block light impinging on or transmitted through the first portion of the discriminator and a second aperture disposed to block light impinging on or transmitted through the second portion of the discriminator.

The method may involve combining image information from the first and second images to generate third and fourth images having a reduced separation between respective perspective viewpoint locations.

The combining may involve scaling an intensity of the first and second images.

In accordance with another aspect of the invention there is provided an apparatus for generating three-dimensional image information using a lens having a single imaging path and an associated field of view. The apparatus includes a lens having a single imaging path operable to direct light captured within a field of view of the lens to an aperture plane of the lens. The apparatus also includes a spatial discriminator located proximate the aperture plane, the discriminator including a first portion disposed to transmit light having a first optical state through a first portion of the single imaging path and a second portion disposed to transmit light having a second optical state through a second portion of the single imaging path. The first and second portions of the single imaging path provide respective first and second perspective viewpoints within the field of view of the lens for forming respective first and second images at an image plane of the lens, the first image representing objects within the field of view from the first perspective viewpoint and the second image representing the objects from the second perspective viewpoint. The first and second images together are operable to represent three dimensional spatial attributes of the objects. The apparatus further includes an image sensor disposed at the image plane of the lens, the image sensor including a first plurality of sensor elements responsive to light having the first optical state, and a second plurality of sensor elements on the image sensor responsive to light having the second optical state.

The image sensor may include first and second pluralities of sensor elements each including a selective element operable to transmit light having a corresponding optical state and to block transmission of light having other than the corresponding optical state, and a corresponding sensor element underlying the selective element.

Each corresponding sensor element may include a plurality of sensor elements.

The respective first and second pluralities of sensor elements may be arranged in a repeating mosaic pattern operable to reduce spatial interference due to a repetition frequency of the sensor elements of the image sensor.

The first portion of the discriminator may include a first polarizer portion disposed to transmit light having a first polarization state through the first portion of the single imaging path and the second portion of the discriminator may include a second polarizer portion disposed to transmit light having a second polarization state through the second portion of the single imaging path.

The image sensor may include a first plurality of sensor elements disposed to transmit light having the first polarization state to a corresponding plurality of sensor elements and to block transmission of light having the second polarization state, and the second plurality of sensor elements are disposed to transmit light having the second polarization state to a corresponding plurality of sensor elements and to block transmission of light having the first polarization state.

The first portion of the polarizer may be operably configured to transmit light having a left-handed elliptical polarization state through the first portion of the polarizer and to transmit light having a right-handed elliptical polarization state through the second portion of the polarizer and the first plurality of image sensor elements may include a first plurality of polarizer elements operable to transmit light having a left-handed elliptical polarization state and to block light having a right-handed elliptical polarization state, and the second plurality of image sensor elements may include a second plurality of polarizer elements operable to transmit light having a right-handed elliptical polarization state and to block light having a left-handed elliptical polarization state.

The first plurality of polarizer elements each may include a quarter wave plate operable to change the right-handed elliptical polarization state to a first linear polarization state and a linear polarizing element operable to transmit light having the first linear polarization state, and the second plurality of polarizer elements each may include a quarter wave plate operable to change the left-handed elliptical polarization state to a second linear polarization state and a linear polarizing element operable to transmit light having the second linear polarization state.

The left-handed elliptical polarization state may include a left-handed circular polarization state and the right-handed elliptical polarization state may include a right-handed circular polarization state.

The first portion of the polarizer may have a first linear polarization orientation and the second portion of the polarizer may have a second linear polarization orientation, the first linear polarization orientation being oriented orthogonal to the second linear polarization orientation and the first plurality of polarizer elements each may include a polarizer element operable to transmit light having a first linear polarization state and to block light having a right-handed elliptical polarization state, and the second plurality of polarizer elements each may include a polarizer element operable to transmit light having a second linear polarization state and to block light having a left-handed elliptical polarization state.

The first linear polarization orientation may be oriented at 45 degrees.

The first plurality of polarizer elements may include a plurality of linear polarizer elements operable to transmit light having the first polarization state, and the second plurality of polarizer elements may include a plurality of linear polarizer elements operable to transmit light having the second polarization state.

The discriminator may be operably configured to be selectively rotated by about 90 degrees to generate images in one of a landscape orientation and a portrait orientation.

The first portion of the discriminator may include a first filter portion disposed to transmit light having first spectral attributes through the first portion of the single imaging path and the second portion of the discriminator may include a second filter portion disposed to transmit light having second spectral attributes through a second portion of the single imaging path, and the first plurality of sensor elements may be operably configured to transmit light having the first spectral attributes and to block transmission of light having the second spectral attributes, and the second plurality of sensor elements are operably configured to transmit light having the second spectral attributes and to block transmission of light having the first spectral attributes.

The first spectral attributes may include a first set of wavelengths and the second spectral attributes may include a second set of wavelengths, the first and second sets of wavelengths being separated in wavelength by a wavelength difference.

Each sensor element may include a plurality of filter elements, each filter element being operable to transmit light in a wavelength range within the set of wavelength ranges.

The plurality of filter elements may be disposed such that light passing through the sensor element passes successively through each of the filter elements before reaching an underlying color filter array.

The plurality of filter elements may be disposed adjacent to each other and overlying corresponding sensor elements and the filter elements are configured to simultaneously generate the first and second images while directing light to corresponding underlying sensor elements for generating color information.

The image sensor may be operably configured to generate an image signal; representing the first and second images, and may further include a controller operably configured to process the imaging signal to generate a first imaging signal representing the first image received by the first plurality of sensor elements and to generate a second imaging signal representing the second image received by the second plurality of sensor elements, and the controller is operably configured to image process the first and second image signals to cause the first and second images to have the same color appearance.

Each of the first and second sets of wavelengths may include red, green, and blue wavelengths and the wavelength difference may include between about 1 nanometer and about 100 nanometers.

The image sensor may include a first plurality of sensor elements having an overlying filter element operable to transmit light having the first spectral attributes and a second plurality of sensor elements having an overlying filter element operable to transmit light having the second spectral attributes.

The filter elements each may include a narrow optical band pass filter having a spectral response corresponding to the respective first and second spectral attributes.

The first portion of the discriminator may include a filter element operable to transmit the first set of wavelengths of light and the second portion of the discriminator may include a filter element operable to transmit the second set of wavelengths of light.

The image sensor may be operably configured to generate an image signal representing the first and second images.

The image sensor may be operably configured to generate a first imaging signal representing the first image received by the first plurality of sensor elements and to generate a second imaging signal representing the second image received by the second plurality of sensor elements.

The image sensor may be operably configured to generate representing light received at each of the first and second pluralities of sensor elements, and to process the imaging signal to generate a first imaging signal representing the first image received by the first plurality of sensor elements and to generate a second imaging signal representing the second image received by the second plurality of sensor elements.

The aperture plane of the lens may include an aperture plane of the lens located at one of a location of a physical aperture of the lens, or a location of a conjugate of the physical aperture.

The discriminator may be displaced from the aperture plane by a sufficiently small displacement such that intensity variations in the first and second images due to vignetting by the first and second portion of the discriminator may be below a threshold that is detectable by the human eye.

The displacement may be sufficiently small to reduce the intensity variations to below 30% across an image plane associated with the first and second images.

The discriminator may include a discriminator coating applied to a surface of a lens element disposed proximate to the aperture plane.

The lens may include a plurality of generally circular lens elements defining a generally circular cross-section single imaging path and the discriminator may include a left half operable to transmit light having the first optical state and a right half operable to transmit light having the second optical state, the respective left and right halves of the discriminator defining respective left and right semicircular portions of the single imaging path.

The lens may include a plurality of generally circular lens elements defining a generally circular cross-section single imaging path and the discriminator may include a left sector portion operable to transmit light having the first optical state and a right sector portion operable to transmit light having the second optical state, the left and right sector portions being disposed about a vertical centerline of the lens.

The discriminator may be operable to vary an extent of the first and second portions of the imaging path to cause the first and second perspective viewpoints to change location while forming the first and second images, the change in perspective viewpoint location providing a corresponding change in the representation of the three dimensional spatial attributes.

The apparatus may include a first aperture disposed to block light impinging on or transmitted through the first portion of the discriminator and a second aperture disposed to block light impinging on or transmitted through the second portion of the discriminator.

The apparatus may include a controller operably configured to combine image information from the first and second images to generate third and fourth images having a reduced separation between respective perspective viewpoint locations.

The controller may be operably configured to combine the image information by scaling an intensity of the first and second images.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention.

DETAILED DESCRIPTION

Figure 1:
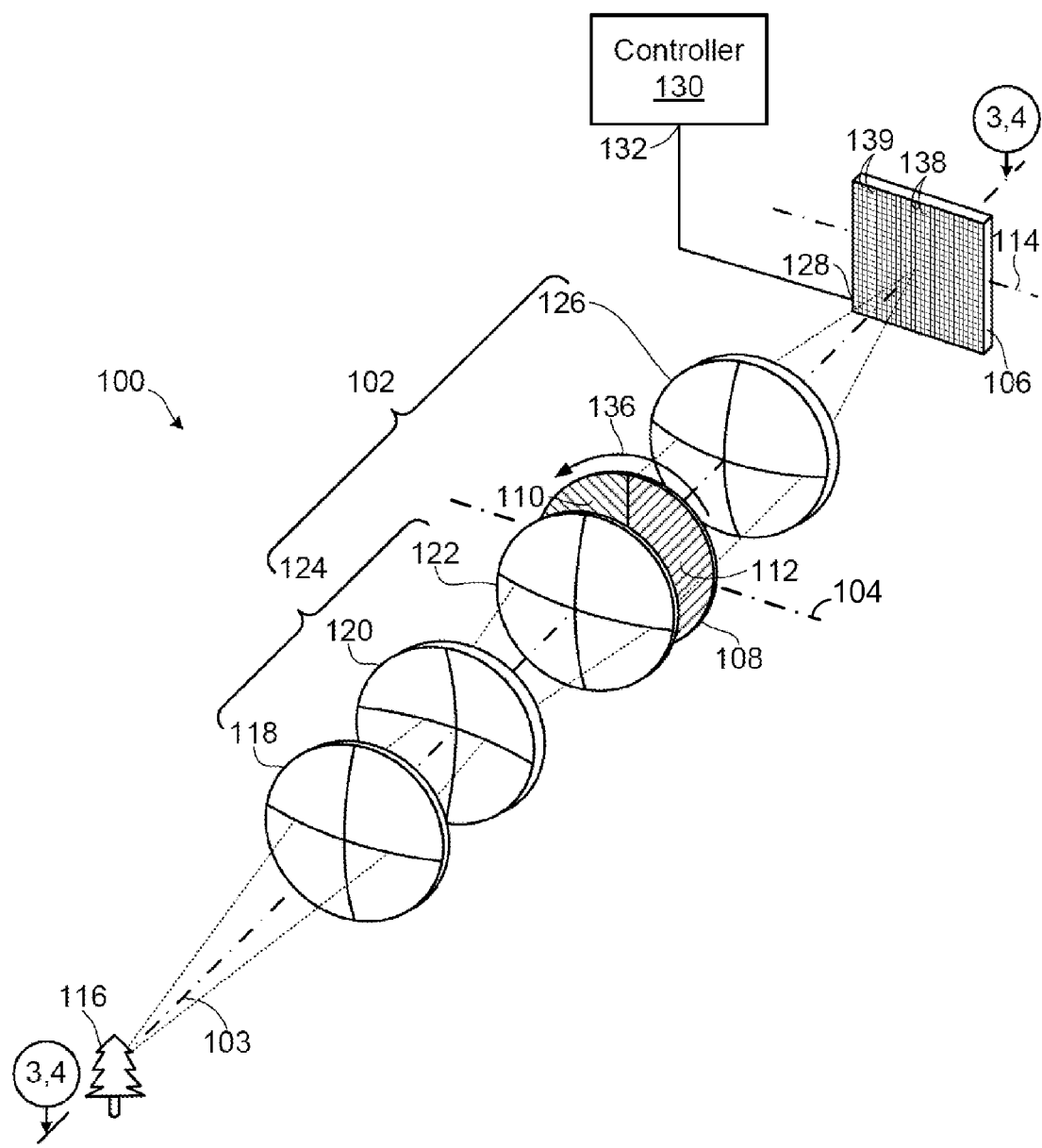
FIG. 1 is a perspective view of an apparatus for generating three-dimensional image information according to a first embodiment of the invention.

Referring to FIG. 1, an apparatus for generating three-dimensional image information according to a first embodiment of the invention is shown generally at 100. The apparatus 100 includes a lens 102 having a single imaging path generally oriented along a central axis 103. The lens 102 is operable to direct light captured within a field of view of the lens to an aperture plane 104 of the lens.

The apparatus 100 also includes a spatial discriminator 108 located proximate the aperture plane 104. The aperture plane 104 may be a physical aperture plane of the lens 102 or may be a conjugate of the aperture plane. The discriminator 108 includes a first portion 110 disposed to transmit light having a first optical state through a first portion of the single imaging path and a second portion 112 disposed to transmit light having a second optical state through a second portion of the single imaging path. The first and second portions 110 and 112 of the single imaging path provide respective first and second perspective viewpoints within the field of view of the lens 102 for forming respective first and second images at an image plane 114 of the lens. The first image represents objects within the field of view (such as the object 116) from the first perspective viewpoint and the second image represents the objects from the second perspective viewpoint. The first and second images together are operable to represent three dimensional spatial attributes of the objects 116.

The apparatus 100 also includes an image sensor 106 disposed at the image plane 114 of the lens 102. The image sensor 106 includes a first plurality of sensor elements 138 responsive to light having the first optical state, and a second plurality of sensor elements 139 responsive to light having the second optical state. The image sensor 106 may be implemented as a charge coupled device sensor (CCD) or an active pixel sensor (such as a CMOS active pixel sensor).

The image sensor 106 includes an output 128 for generating an image signal. The apparatus 100 also includes a controller 130 having an input 132 for receiving the image signal from the output 128 of the image sensor. In one embodiment, output 128 may comprise a plurality of parallel signal lines to enable parallel readout of the image signal from the image sensor 106. The controller may include a processor circuit operably configured to perform processing of the image signal.

In the embodiment shown in FIG. 1, the lens 102 includes a plurality of lens elements including lens elements 118, 120, and 122, which make up a zoom lens group 124 and define the location of the aperture plane 104. The focal length of the zoom lens group 124 may be varied by moving lens elements 118 and 120. The lens 102 also includes a focusing lens 126 for focusing the images at the image plane 114. In other embodiments, the lens 102 may be made of a greater or lesser number of lens elements and may be a prime, telephoto, or other type of lens used in imaging.

Figure 2:
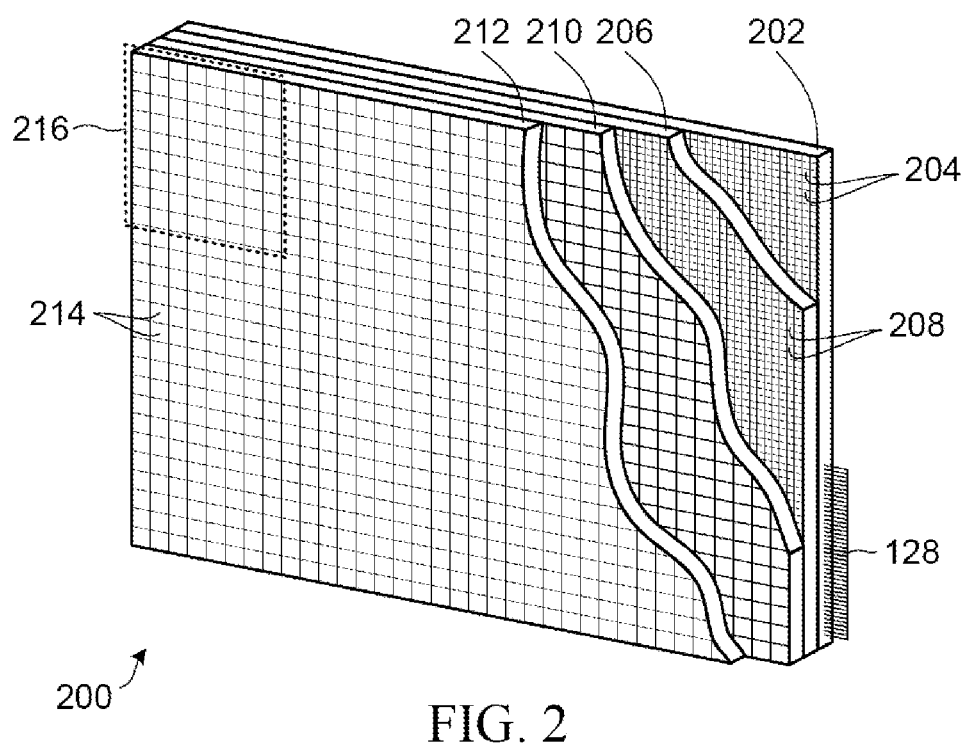
FIG. 2 is a partially cut away perspective view of an image sensor used in the apparatus shown in FIG. 1.

Referring to FIG. 2, an image sensor in accordance with a first embodiment of the invention is shown generally at 200. The image sensor 200 includes a photosensitive layer 202 including a plurality of sensor elements 204 that are operable to produce an electrical charge or voltage representing a photon flux incident on the sensor element during a period of time. The image sensor 200 further includes a color filter array 206 overlying the photosensitive layer 202 and having a plurality of color filter elements 208. Each of the color filter elements 208 overlies a sensor element 204 to provide a one-to-one correspondence between color filter elements and sensor elements. Layers 202 and 206 together may comprise a CCD image sensor or CMOS active pixel sensor, similar to conventional image sensors.

The image sensor 200 also includes selective layers 210 and 212. In one embodiment the layers 210 and 212 include selective elements 214 that are operable to selectively transmit light having a one of the first and second optical states, and to block transmission of light having the other optical state.

Figure 3:
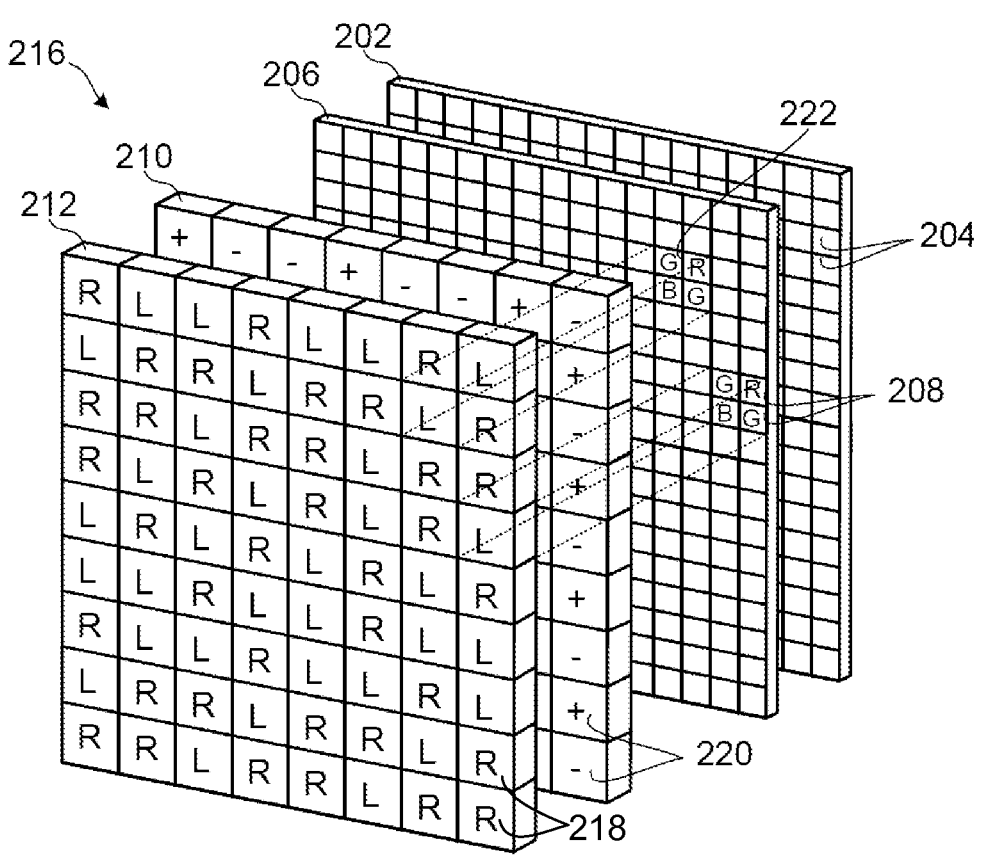
FIG. 3 is an exploded view of a portion of the image sensor shown in FIG. 2.

A portion 216 of the image sensor 200 in accordance with one embodiment of the invention is shown in exploded view in FIG. 3. Referring to FIG. 3, in this embodiment each selective element 214 includes a quarter wave plate element 218 on layer 212 and a linear polarizer element 220 on layer 210. In FIG. 3, some of the quarter wave plates 218 on layer 212 are marked as "R", indicating that the wave plate is oriented to change right-hand circular polarized light to linear polarized light having a first polarization orientation (for example −45°. Other quarter wave plates 218 on layer 212 are marked as "L", indicating that the wave plate is oriented to change left-handed circular polarized light to linear polarized light (for example +45°. Similarly, some of the linear polarizers 220 on layer 210 are marked as "−", indicating that the polarizer is oriented to transmit linear polarized light having a first polarization orientation (for example −45° and others of the linear polarizers on layer 210 are marked as "+", indicating that the polarizer is oriented to transmit linear polarized light having a second polarization orientation (for example +45°.

The wave plates 218 and polarizers 220 are substantially the same size and each wave plate marked "R" overlies a polarizer marked as "−" and each wave plate marked "L" overlies a polarizer marked as "+". The wave plates 218 and polarizers 220 may be fabricated by conventional lithographic deposition or processes, for example.

The color filter array layer 206 comprises the plurality of color filter elements 208, which in this embodiment are arranged in a Bayer filter pattern having two green or luminance sensitive elements (G), a red chrominance-sensitive element (R) and a blue chrominance-sensitive element (B). Each of the G, R and B color filter elements 208 is a quarter of the size of the selective elements 214 (made up of a quarter wave plate element 218 and linear polarizer element 220) such that a Bayer cell 222 of four color filter elements (GRBG) have the same size as a single selective element and underlies the corresponding selective element.

Finally, the plurality of sensor elements 204 on the photosensitive layer 202 each have a size and alignment corresponding to an overlying color filter element 208. A spectral response of the sensor elements 204 is thus modified by the overlying color filter element 208, to permit color information in the images to be recovered from the image signal.

Spatial Discriminator

Generally, light received from the field of view of the lens 102 will have random linear polarization. In one embodiment the first portion 110 of the spatial discriminator 108 may comprise a linear polarizer followed by a quarter wave plate. The linear polarizer may be oriented such that linearly polarized light components incident on the linear polarizer and having a first polarization orientation (for example −45° are transmitted through the linear polarizer. The quarter wave plate is oriented to cause the light having a −45° polarization orientation to undergo a change to left-handed circular polarized light. The first portion 110 of the discriminator in this embodiment would thus result in left-handed circular polarized light being transmitted.

Similarly, the second portion 112 of the spatial discriminator 108 may also comprise a linear polarizer oriented such that linearly polarized light components incident on the linear polarizer and having a second polarization orientation (for example +45° are transmitted through the linear polarizer. The quarter wave plate is oriented to cause the light having a +45° polarization orientation to undergo a change to right-handed circular polarized light. The second portion 112 of the discriminator in this embodiment would thus result in right-handed circular polarized light being transmitted.

Operation

Figure 4:
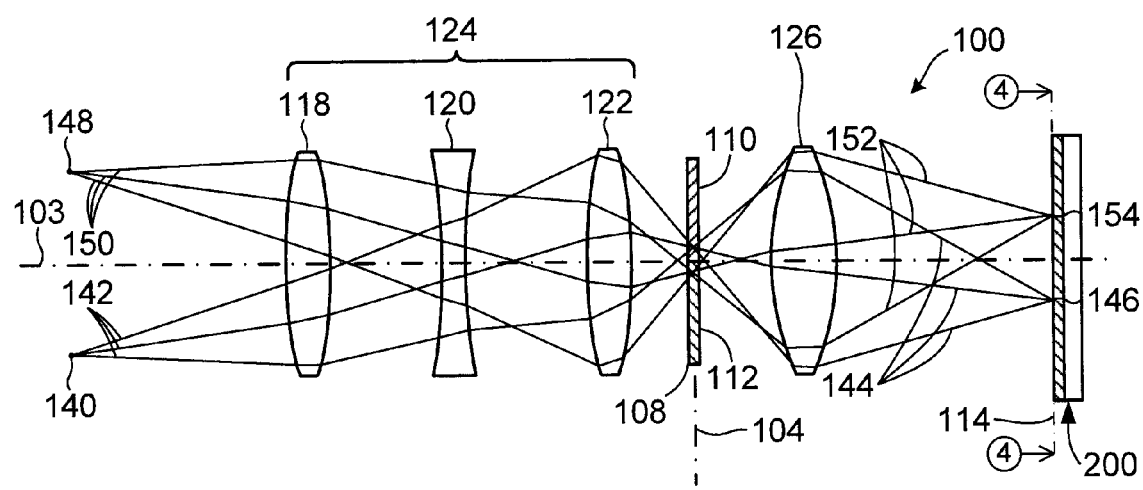
FIG. 4 is a top view depicting an operational state of the of the apparatus shown in FIG. 1.
Figure 5:
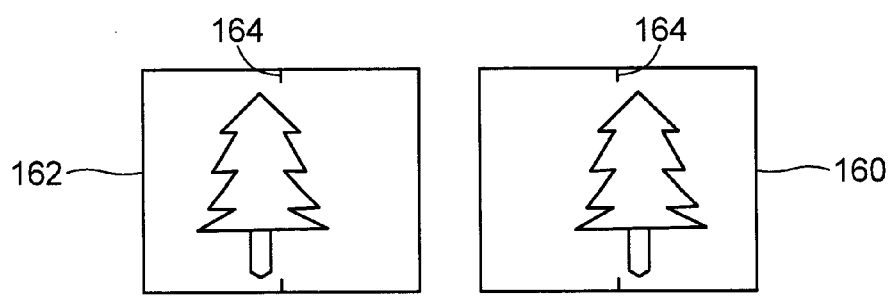
FIG. 5 is a schematic view representing images generated by the apparatus shown in FIG. 4.

Operation of the image sensor 200 shown in FIG. 2 and FIG. 3 is described with further reference to FIG. 4 and FIG. 5, which show the apparatus 100 in top view.

Referring to FIG. 4, light rays 142 emanating from a first point 140 in the field of view of the lens 102 may include randomly polarized light, which is captured by the lens 102 and directed to the aperture plane 104 where the rays pass through the first portion 110 of the discriminator 108. Light rays 144 transmitted through the portion 110 of the discriminator 108 have left-handed circular polarization and are focused to a point 146 on the image plane 114. Referring back to FIG. 3, light rays having a left-handed circular polarization that impinge on quarter wave plates 218 on layer 212 marked as "L" undergo a change in polarization state from left-handed circular polarized light to +45° linear polarized light. The linear polarizer elements 220 marked "+" transmit the +45° polarized light through corresponding color filter elements 208 and sensor elements 204 to facilitate recording of the first image. Light rays having a right-handed circular polarization that impinge on quarter wave plates 218 on layer 212 marked as "L" undergo a change in polarization state from right-handed circular polarized light to −45° linear polarized light and are blocked by the linear polarizer elements marked as "+".

Referring back to FIG. 4, light rays 150 emanating from a second point 148 in the field is captured by the lens 102 and directed to the aperture plane 104 where the rays pass through the second portion 112 of the discriminator 108. Light rays 152 transmitted through the portion 112 of the discriminator 108 have right-handed circular polarization and are focused to a point 154 on the image plane 114. Referring back to FIG. 3, light rays having a right-handed circular polarization that impinge on quarter wave plates 218 on layer 212 marked as "R" undergo a change in polarization state from right-handed circular polarized light to −45° linear polarized light. The linear polarizer elements 220 marked "−" transmit the −45° polarized light through corresponding color filter elements 208 and sensor elements 204 to facilitate recording of the second image. Light rays having a left-handed circular polarization that impinge on quarter wave plates 218 on layer 212 marked as "R" undergo a change in polarization state from right-handed circular polarized light to +45° linear polarized light and are blocked by the linear polarizer elements marked as "−".

Advantageously, the first and second images are concurrently available at the image sensor element 204 and may be separated by reading out signal values accumulated in the sensor elements 204 during a time period. For video images the time period may be set by a desired frame rate (for example 30 frames per second for NTSC video signals). In one embodiment, all sensor elements are read out of the image sensor 200 as a stream of pixels in a single operation and the controller 130 (shown in FIG. 1) separates the pixels into first image pixels and second image pixels in accordance with the specific arrangement of the selective elements 214 on the selective layers 210 and 212 of the image sensor 200. In other embodiments, sensor elements associate with the first image may be read out during a first time period, while sensor elements associate with the second image may be read out during a second time period.

Referring to FIG. 5, exemplary first and second images of the object 116 shown in FIG. 1 are shown at 160 and 162. Since the first portion of the single imaging path defined by the first portion 110 of the discriminator 108 is offset from a central axis 103, the first image 160 has a perspective viewpoint from one side of the object 116 and is offset toward the left from an image center 164. The second image 162 has a perspective viewpoint from the other side of the object 116 and is formed offset toward the right from the image center 164. When the first and second images 160 and 162 are selectively directed to respective left and right eyes of a user, the user will be able to discern 3D information from the images, in much the same way that the user would be able to discern 3D information when viewing the actual object 116.

The first and second images 160 and 162 may be alternately displayed as separate video fields on a video display monitor. Various types of active and passive eyewear are available for directing such displayed first and second images 160 and 162 to the user's eyes. Passive types of eyewear generally rely on additional wavelength or polarization processing of the displayed images to enable passive filter elements in the eyewear to separate the images. Active types of eyewear generally include a receiver for receiving a synchronization signal from a display to alternatively permit transmission of the first and second images 160 and 162 to the respective left and right eyes. Alternatively, the first and second images 160 and 162 may be processed to match up identifiable features in the respective images and to determine lateral shifts between the identified features. The determined lateral shifts, along with knowledge of the imaging parameters of the apparatus 100, may be used to calculate a difference in depth between points on an object or between objects at different depths.

Advantageously, the discriminator 108 may be a passive element such as a passive polarizer element, which permits use of relatively thin materials such as an absorptive polarizer film or thin film polarizer. Such materials permit the discriminator 108 to be placed very close to or at the aperture plane 104, even in a lens 102 that has limited space between lens elements. It is advantageous to have selective transmission/blocking of the light for producing the first and second images occurring at least proximate an aperture plane of the lens 102 to reduce or eliminate vignetting of the images due to the selective transmission of light through the first or second portions of the single imaging path. In some embodiments, the discriminator 108 may be located proximate an iris (not shown) of the lens that defines the system aperture and controls an amount of light captured by the lens 102. Alternatively, the first and second portions 110 and 112 of the discriminator 108 may be applied directly as a coating to a lens element defining an aperture plane of a lens, or a lens element that is located proximate the aperture plane of the lens.

To achieve a desired imaging quality or performance using a particular lens, an optical sensitivity analysis may be performed to yield a distance tolerance representing a maximum displacement of the discriminator 108 from the aperture plane 104. Such an analysis may take into account geometric offsets in the first and second images due to vignetting due to the first and second portions 110 and 112 of the discriminator 108, and the distance tolerance would provide a maximum distance from the aperture plane to satisfy a criterion for acceptable 3D imaging quality. The degree to which imaging quality is affected by moving the discriminator 108 away from the aperture plane is dependent on the configuration of the lens elements making up the lens 102 and the desired imaging performance of the system. In very high performance imaging systems, the discriminator 108 may have to be located very close to the aperture plane 104 to minimize vignetting and thus provide first and second images having substantially uniform image intensity across the image. In lower performance imaging systems, it may be acceptable to permit quite significant image intensity falloff at edges of the images since the human eye is not extremely sensitive to such falloff. In non-critical imaging applications a 30% to 90% image falloff at the outer edges of an image may be acceptable and may be compensated by computer image processing or other optical processes.

Referring back to FIG. 3, in the embodiment shown the "R" and "L" quarter wave plates 218 are repeated in a mosaic pattern. In the embodiment shown a first row has a repeating pattern "RLLRLLR" and a second row has a repeating pattern "LRRLRRL". Various other repeating mosaic patterns may be used. The repeating mosaic pattern is operable to reduce spatial interference effects such as moiré, which may occur when a regular repeating pattern is used.

Alternatively, in another embodiment the discriminator 108 may be configured as a linear polarizer having the first portion 110 configured to transmit −45° polarized light, and the second portion 110 configured to transmit +45° polarized light. In this embodiment the selective layer 212 is not required and the nelements 220 on the layer 210 will perform the function of the selective elemets. In such an embodiment, when oriented as shown in FIG. 1, the apparatus 100 is configured to generate images in what is commonly referred to as "landscape orientation" (i.e. the longest dimension of the image is horizontally oriented). The resulting first and second images are separated into right and left images, which advantageously causes the first and second images to correspond to images that would usually be viewed by a user's horizontally separated right and left eyes. However, particularly in still image photography, it is common for users of a camera to capture images in both landscape orientation and portrait orientation (i.e. where the longer dimension of the image is vertically oriented). In an alternative embodiment of the apparatus 100, the apparatus may be configured to permit configuration in either a landscape mode or a portrait mode. Specifically, the discriminator 108 may be rotated by about 90 degrees in the direction indicated by the arrow 136, such that the first and second images are vertically separated in the orientation of the apparatus as shown in FIG. 1. In this configuration, when the apparatus 100 is oriented to capture images in portrait mode, the first and second images would remain horizontally separated, thus providing first and second images having respective right and left perspective viewpoints. The about 90 degree rotation of the discriminator 108 may be implemented using a mechanical rotator having an actuator that is manually operated by the user. Alternatively, the mechanical rotator may be actuated by an electric motor either in response to user selection of a portrait mode, or automatically in response to an orientation signal generated by an orientation sensor such as an accelerometer or gravity sensor (not shown).

In the embodiment shown in FIG. 3 and FIG. 4 the first and second polarization orientations are respectively at −45° and +45° to vertical but in other embodiments the polarizations may be otherwise oriented (for example vertically and horizontally). Advantageously, orienting the first and second polarization orientations at ±45° prevents differences between the first and second images due to light received from the field of view of the lens 102 being partially polarized, as would occur when light reflects off surfaces such as a roadway or body of water, for example.

In another embodiment, the first portion 110 of the discriminator 108 may include a polarizer operable to transmit light having a left-handed elliptical polarization state and the second portion 112 of the discriminator 108 may include a polarizer operable to transmit light having a right-handed elliptical polarization state.

Spectral Discriminator Embodiment

In other embodiments the portions 110 and 112 of the discriminator 108 may be replaced with filters or other optical elements that operate on another property or state of light to generate the first and second images. For example, the first portion 110 of the discriminator 108 may include a first filter portion disposed to transmit light having first spectral attributes through the first portion of the single imaging path and the second portion of the discriminator may include a second filter portion disposed to transmit light having second spectral attributes through a second portion of the single imaging path. In this embodiment a first plurality of selective elements of the image sensor 200 would be correspondingly configured to form the first image by transmitting light having the first spectral attributes and blocking transmission of light having the second spectral attributes. Similarly, a second plurality of selective elements of the image sensor 200 would be correspondingly configured to form the second image by transmitting light having the second spectral attributes and blocking transmission of light having the first spectral attributes.

Figure 6:
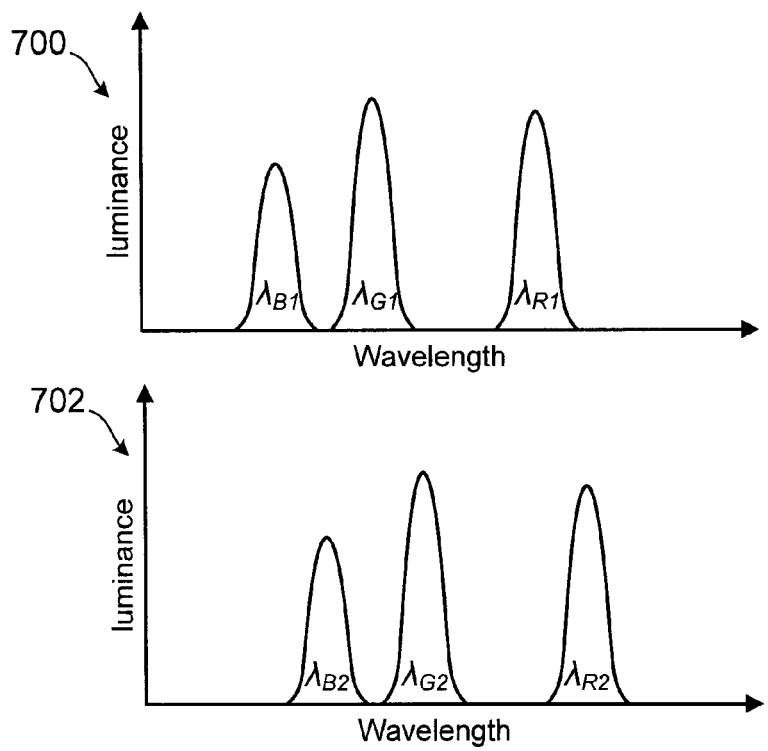
FIG. 6 is a graphic depiction of transmission spectra for an interference filter used in an alternative embodiment of the apparatus shown in FIG. 1 to FIG. 4.

Referring to FIG. 6, the portions 110 and 112 may be implemented as interference filters that transmit specific narrow bands of wavelengths, such as blue, green, and red light. Transmission spectra for such interference filters are shown graphically in FIG. 6 at 700 and 702. The first portion 110 of the discriminator 108 may be configured to transmit a first plurality of wavelengths $\lambda_{B1}$, $\lambda_{G1}$, and $\lambda_{R1}$ as shown at 700 and the second portion 112 may be configured to pass a second plurality of wavelengths $\lambda_{B2}$, $\lambda_{G2}$, and $\lambda_{R2}$ as shown at 702.

Figure 7:
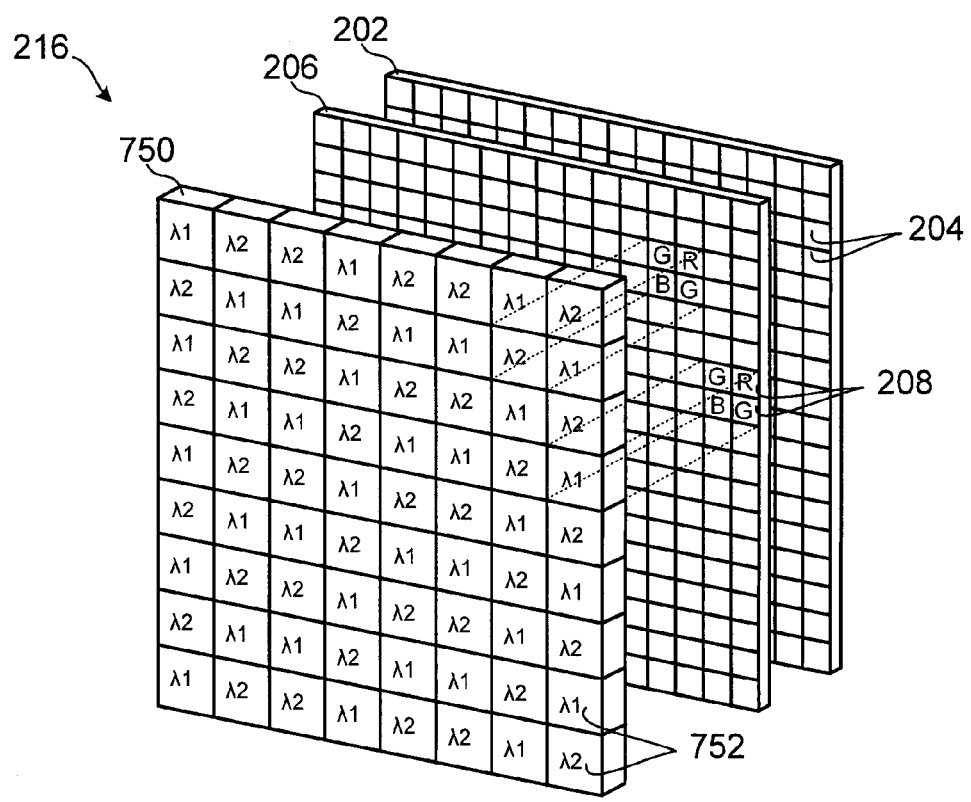
FIG. 7 is an exploded view of a portion of the image sensor shown in FIG. 2 in accordance with an alternative embodiment of the invention.

Referring to FIG. 7, the portion 216 of an image sensor 200 in accordance with the present embodiment may be configured such that the selective layers 212 and 210 are replaced by a selective layer 750. The selective layer 750 includes selective elements 752, which are marked as $\lambda_1$ in FIG. 7 and are responsive to the first plurality of wavelengths. The selective layer 750 also includes selective elements 752, which are marked as $\lambda_2$ and are responsive to the second plurality of wavelengths. The selective elements may comprise of absorptive, interference filters, or a combination of these, where the filter is responsive to only a very narrow band of wavelengths. In other embodiments, the filters may be fabricated to provide a sharp wavelength transition at edges of the transmission bands, thereby accommodating more than three wavelength ranges in each of the first and second plurality of wavelengths.

When the second plurality of wavelengths 702 are received through the single imaging path, the portion 110 blocks these wavelengths while the portion 112 transmits the second plurality of wavelengths, which are imaged to form a first image at the image plane 114. When the first plurality of wavelengths 700 are received through the single imaging path, the portion 112 blocks these wavelengths while the portion 110 transmits the first plurality of wavelengths, which are imaged to form a second image at the image plane 114. The selective elements 752 have substantially the same spectral response as the corresponding first and second portions of the discriminator 108 and, thus the selective layer 750 transmits respective wavelength to the underlying plurality of color filter elements 208 and plurality of sensor elements 204, thus facilitating recording of the first and second images.

The first and second images may then be processed to re-construct the color of the images such that the human eye perceives a color gamut that would have been perceived if the filters were not present in the system. The process would generally be analogous to the processing used to reconstruct color in conventional cameras that use a Bayer color filter array. The wavelength difference could be between about 1 and about 100 nanometers. Such image processing may involve changing the relative intensities of specific wavelengths in the first and second plurality of wavelengths such that a user would not be able to discern a spectral difference between the two images even though the images have slightly offset spectra.

In the embodiment shown in FIG. 7, each $\lambda_1$ selective element 752 includes a filter operable to filter each of the wavelength ranges shown at 700 in FIG. 6, and each of the $\lambda_2$ selective element 752 includes a filter operable to filter each of the wavelength ranges shown at 702 in FIG. 6. Such filters may thus include three separate filter layers, each layer being tailored to filter one of the wavelength ranges shown at 750 and 752.

In another embodiment, the color filter array 206 may be omitted and each selective elements 752 may be configured to perform the function of the color filter array. For example, each $\lambda_1$ selective element 752 may include four adjacently disposed filter elements, for example a $\lambda_{B1}$, and $\lambda_{R1}$ and two $\lambda_{G1}$ elements (for the case of a Bayer type color filter array). Similarly, each $\lambda_2$ selective element 752 may also include four adjacently disposed filter elements, for example a $\lambda_{B2}$ and $\lambda_R$ and two $\lambda_{G2}$ elements. Advantageously, such an embodiment may be used to incorporate both color separation functions and image separation functions into a single suitably configured layer.

Variable Steropsis

Figure 8:
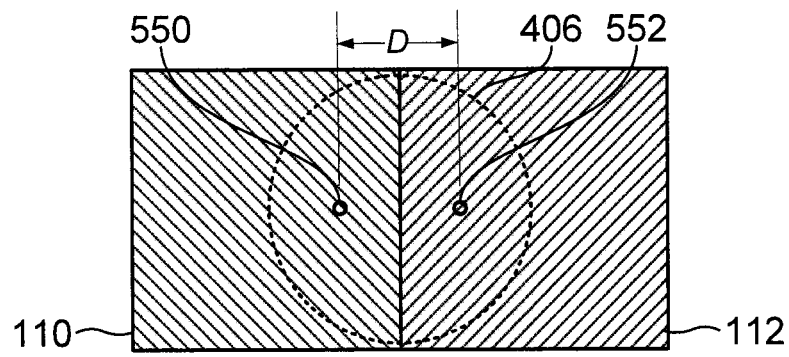
FIGS. 8-10 are a series of views showing an alternative embodiment of a polarizer used in the apparatus shown in FIG. 1.
Figure 9:
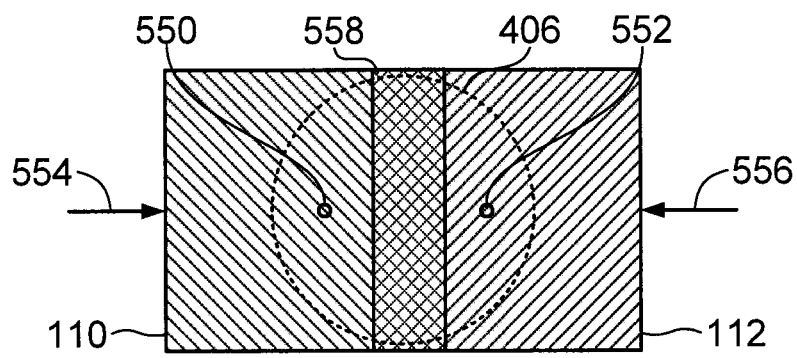
Figure 10:
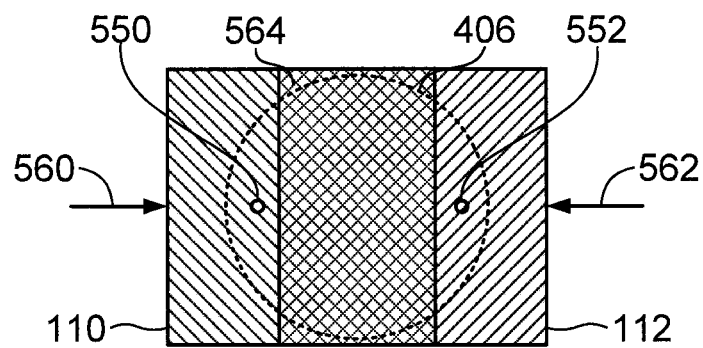

In the embodiments shown in FIG. 1 and FIG. 3, the single imaging path is circular in shape and the first portion 110 of the discriminator 108 extends to cover a first semicircular portion of the imaging path, while the second portion 112 extends to cover a second semicircular portion of the imaging path. In an embodiment where the first and second portions 110 and 112 are configured as linear polarizers (for example −45° and +45°, the portions may each extend to cover a sector of the single imaging path of less then a semicircular area as shown in FIG. 8, FIG. 9 and FIG. 10. Referring to FIG. 8, the discriminator 108 may be sized such that the first and second portions 110 and 112 extend outwardly beyond the imaging path 406. A centroid of the area of the single imaging path (indicated by broken line 406) covered by the first portion 110 is shown at 550 and a centroid of the area of the single imaging path covered by the second portion 112 is shown at 552. The centroids 550 and 552 may be viewed as defining a center of perspective for the respective first and second images formed through a lens, such as the lens 102 shown in FIG. 1. A distance D between the two centroids 550 and 552 represents the steroptic separation between images, which loosely equates to an "amount of 3D" generated by the apparatus.

Referring to FIG. 9, by moving the first portion 110 of the discriminator 108 inwardly in the direction of the arrow 554 and the second portion 112 inwardly in the direction of the arrow 556, an overlapping region 558 is formed between the two polarizer portions. Light passing through the overlapping region 558 will pass through both a portion of the discriminator 108 having a −45° polarization orientation and a portion having a +45° polarization orientation and will thus be blocked regardless of polarization orientation. Under these conditions the centroids 550 and 552 are each shifted outwardly and thus the perspective viewpoint is also shifted outwardly providing greater steroptic separation between the first and second images.

Referring to FIG. 10, further movement of the first portion 110 of the discriminator 108 inwardly in the direction of the arrow 560 and the second portion 112 inwardly in the direction of the arrow 562, causes the overlapping region 564 between the two polarizer portions to increase in extent. Light passing through the overlapping region 564 will again pass through both −45° and +45° polarizing portions of the discriminator 108 and will thus be blocked. Under these conditions the centroids 550 and 552 are again shifted outwardly thus further changing the perspective viewpoint.

In one embodiment, the movements of the portions 110 and 112 of the discriminator 108 may be performed by an actuator such as a mini stepper motor and the degree of separation of the centroids may be varied while the first and second images are being formed to provide for variable steropsis as disclosed in commonly owned PCT patent application PCT/CA2009/000957, filed on Jul. 10, 2009, entitled "METHOD AND APPARATUS FOR GENERATING THREE DIMENSIONAL IMAGE INFORMATION USING A SINGLE IMAGING PATH", which is incorporated herein by reference in its entirety.

In another embodiment, the first and second images formed by respective first and second portions 110 and 112 of the discriminator 108 may used to generate third and fourth images by combining the first and second images. For example, with the first and second portions 110 and 112 of the discriminator 108 disposed as shown in any of FIG. 8, 9, or 10, portions of the first and second images may be combined on some basis to generate the third image. Similarly, portions of the first and second images may be combined on another basis to generate the fourth image. In one embodiment, the basis of combination may be scaling an intensity of the first image by a first ratio and scaling an intensity the second image by a second ratio and then normalizing and combining the scaled images to generate the third image. Similarly, the fourth image may be generated by scaling an intensity of the first image by the second ratio and scaling an intensity of the second image by the first ratio, and then normalizing and combining the scaled images to form the fourth image.

Including a portion or proportion of the first and second images, effectively reduces the steroptic separation between the third and fourth images. The processing may be performed by the controller 130 (shown in FIG. 1) and may be used to further reduce the steroptic separation from that provided in any of FIGS. 8-10. Such changes may be used to provide a transition from weak or no steroptic separation (i.e. essentially 2D) to stronger steroptic separation for 3D image generation.

In an alternative embodiment, the first and second portions 110 and 112 of the spatial discriminator 108 (shown in FIG. 1) may include respective first and second adjustable apertures (not shown) overlying the respective portions. The apertures facilitate selection of corresponding first and second portions of the single image path for forming the first and second images. Advantageously, incorporation of suitably configured apertures permit the first and second images to be formed using only a portion of the area of the first and second portions 110 and 112 of the discriminator 108. For example, it may be desired to increase a depth of focus in the first and second images by changing the numerical aperture conditions for the respective first and second portions of the single image path. The change in numerical aperture may be achieved by reducing a size of the first and second apertures to block part of the respective portions of the imaging path. In one embodiment the apertures may be implemented as actuated mechanical apertures, such as a mechanical iris. In other embodiments the apertures may be implemented as an electro-optical aperture, for example by using a liquid crystal material. The electronic aperture may be implemented as part of the discriminator 108.

Advantageously, the embodiments disclosed herein facilitate generation of 3D image information using a single imaging path. Furthermore, separation of the first and second images occurs at the image sensor and the images are simultaneously available at the image sensor, thus facilitating video image capture at higher frame rates than for systems that separate images in time.

While specific embodiments of the invention have been described and illustrated, such embodiments should be considered illustrative of the invention only and not as limiting the invention as construed in accordance with the accompanying claims.

What is claimed is:

1. A method for generating three-dimensional image information using a lens having a single imaging path and an associated field of view, the method comprising:
    directing light captured within the field of view of the lens to an aperture plane of the lens;
    receiving said captured light at a spatial discriminator located proximate said aperture plane, said discriminator including a first portion disposed to transmit light having a first optical state through a first portion of the single imaging path and a second portion disposed to transmit light having a second optical state through a second portion of the single imaging path, said first and second portions of said single imaging path providing respective first and second perspective viewpoints within the field of view of the lens for forming respective first and second images at an image sensor disposed at an image plane of said lens, said first image representing objects within the field of view from said first perspective viewpoint and said second image representing said objects from said second perspective viewpoint, said first and second images together being operable to represent three dimensional spatial attributes of said objects;
    receiving said first image at a first plurality of selective elements on said image sensor, each of said first plurality of selective elements overlying at least one sensor element of said image sensor and being configured to transmit light having said first optical state; and
    receiving said second image at a second plurality of selective elements on said image sensor, each of said second plurality of selective elements overlying at least one sensor element of said image sensor and being configured to transmit light having said second optical state.

2. The method of claim 1 wherein said first portion of said discriminator comprises a first polarizer portion disposed to transmit light having a first polarization state through said first portion of the single imaging path and wherein said second portion of said discriminator comprises a second polarizer portion disposed to transmit light having a second polarization state through said second portion of the single imaging path and wherein:
    receiving said first image comprises receiving said first image at a first plurality of selective elements disposed to transmit light received from said first polarizer portion to a corresponding plurality of sensor elements and to block light received from said second polarizer portion; and
    receiving said second image comprises receiving said second image at a second plurality of selective elements disposed to transmit light received from said second polarizer portion to a corresponding plurality of sensor elements and to block light received from said first polarizer portion.

3. The method of claim 2 wherein:
    receiving said captured light comprises receiving light having a left-handed elliptical polarization state through said first portion of said polarizer and receiving light having a right-handed elliptical polarization state through said second portion of said polarizer; and each selective element comprises:
a quarter-wave plate configured to render linearly polarized one of light received from said first portion of said discriminator and light received from said second portion of said discriminator; and
a linear polarizer between said quarter-wave plate and said at least one sensor element, said linear polarizer disposed to transmit one of light from said first portion of said discriminator and light received from said second portion of said discriminator.

4. The method of claim 3 wherein said left-handed elliptical polarization state comprises a left-handed circular polarization state and wherein said right-handed elliptical polarization state comprises a right-handed circular polarization state.

5. The method of claim 2 wherein receiving said captured light comprises receiving light having a first linear polarization orientation through said first portion of said polarizer and receiving light having a second linear polarization orientation through said second portion of said polarizer, said first linear polarization orientation being oriented orthogonal to said second linear polarization orientation and wherein:
receiving said first image at said first plurality of polarizer elements comprises receiving said first image at a plurality of polarizer elements disposed to transmit light having said first linear polarization state and to block light having said second linear polarization state; and
receiving said second image at said second plurality of polarizer elements comprises receiving said second image at a plurality of polarizer elements disposed to transmit light having said second linear polarization state and to block light having said second linear polarization state.

6. The method of claim 1 wherein said first portion of said discriminator comprises a first filter portion configured to transmit light having a first set of wavelengths through the first portion of the single imaging path while blocking light of a second set of wavelengths and wherein said second portion of said discriminator comprises a second filter portion configured to transmit light having a second set of wavelengths through a second portion of the single imaging path while blocking light of said first set of wavelengths, and wherein:
receiving said first image comprises receiving said first image at a first plurality of selective elements operable to transmit light having at least one of said first set of wavelengths while blocking light having any of said second set of wavelengths;
receiving said second image comprises receiving said second image at a second plurality of selective elements operable to transmit light having at least one of said second set of wavelengths while blocking light having any of said first set of wavelengths; and
each of said first and second sets of wavelengths includes red, green and blue wavelengths.

7. The method of claim 6 wherein:
each one of said first plurality of selective elements overlies one sensor element and is operably configured to transmit light having one of said first set of wavelengths while blocking light having any other of said first and second sets of wavelengths; and each one of said second plurality of selective elements overlies one sensor element and is operably configured to transmit light having one of said second set of wavelengths while blocking light having any other of said first and second sets of wavelengths.

8. The method of claim 6 wherein:
each one of said first plurality of selective elements overlies a plurality of sensor elements and is operably configured to transmit light having said first set of wavelengths; and
each one of said second plurality of selective elements overlies a plurality of sensor elements and is operably configured to transmit light having said second set of wavelengths.

9. The method of claim 6 further comprising:
generating an image signal representing said first and second images; and
processing said imaging signal to generate a first imaging signal representing said first image received by said first plurality of sensor elements and to generate a second imaging signal representing said second image received by said second plurality of sensor elements, and wherein said processing comprises processing the first and second image signals to cause the first and second images to have the same color appearance.

10. The method of claim 1 further comprising combining image information from the first and second images to generate third and fourth images having a reduced separation between respective perspective viewpoint locations.

11. The method of claim 10 wherein said combining comprises scaling an intensity of said first and second images.

12. An apparatus for generating three-dimensional image information using a lens having a single imaging path and an associated field of view, the apparatus comprising:
a lens having a single imaging path operable to direct light captured within a field of view of the lens to an aperture plane of the lens;
a spatial discriminator located proximate said aperture plane, said discriminator including a first portion disposed to transmit light having a first optical state through a first portion of the single imaging path and a second portion disposed to transmit light having a second optical state through a second portion of the single imaging path, said first and second portions of said single imaging path providing respective first and second perspective viewpoints within the field of view of the lens for forming respective first and second images at an image plane of the lens, said first image representing objects within the field of view from said first perspective viewpoint and said second image representing said objects from said second perspective viewpoint, said first and second images together being operable to represent three dimensional spatial attributes of said objects; and
an image sensor disposed at said image plane of said lens, said image sensor comprising a first plurality of selective elements transmissive to light having said first optical state, and a second plurality of selective elements on said image sensor transmissive to light having said second optical state, each selective element overlying at least one sensor element of said image sensor.

13. The apparatus of claim 12 wherein:
said first portion of said discriminator comprises a first polarizer portion disposed to transmit light having a first polarization state through said first portion of the single imaging path;

said second portion of said discriminator comprises a second polarizer portion disposed to transmit light having a second polarization state through said second portion of the single imaging path;

said first plurality of selective elements is disposed to transmit light received from said first polarizer portion to a corresponding plurality of sensor elements and to block light received from said second polarizer portion; and said second plurality of selective elements is disposed to transmit light received from said second polarizer portion to a corresponding plurality of sensor elements and to block light received from said first polarizer portion.

14. The apparatus of claim 13 wherein:

said first polarization state is left-handed elliptical polarization and said second polarization state is right-handed elliptical polarization; and each selective element comprises a quarter-wave plate disposed to render linearly polarized one of light received from said first portion of said discriminator and light received from said second portion of said discriminator; and a linear polarizer between said quarter-wave plate and said at least one sensor element, said linear polarizer disposed to transmit one of light from said first portion of said discriminator and light received from said second portion of said discriminator.

15. The apparatus of claim 14 wherein said left-handed elliptical polarization state comprises a left-handed circular polarization state and wherein said right-handed elliptical polarization state comprises a right-handed circular polarization state.

16. The apparatus of claim 13 wherein said first polarization state is a first linear polarization orientation and said second polarization state is a second linear polarization orientation, said first linear polarization orientation being oriented orthogonal to said second linear polarization orientation and wherein:

said first plurality of selective elements each comprises a polarizer element disposed to transmit light having the first linear polarization state and to block light having the second polarization state; and said second plurality of selective elements each comprises a polarizer element disposed to transmit light having the second linear polarization state and to block light having the second polarization state.

17. The apparatus of claim 16 wherein said first linear polarization orientation is oriented at one of −45 degrees and +45 degrees with respect to vertical.

18. The apparatus of claim 12 wherein said discriminator is operably configured to be selectively rotated by one of about +90 degrees and about −90 degrees to generate images in one of a landscape orientation and a portrait orientation.

19. The apparatus of claim 12 wherein:

said first portion of said discriminator comprises a first filter portion disposed to transmit light having a first set of wavelengths through the first portion of the single imaging path while blocking light of a second set of wavelengths;

said second portion of said discriminator comprises a second filter portion disposed to transmit light having the second set of wavelengths through a second portion of the single imaging path while blocking light of said first set of wavelengths;

said first plurality of selective elements is transmissive to light having at least one of said first set of wavelengths while blocking light having any of said second set of wavelengths;

said second plurality of selective elements is transmissive to light having at least one of said second set of wavelengths while blocking light having any of said first set of wavelengths; and each of said first and second sets of wavelengths includes red, green and blue wavelengths.

20. The apparatus of claim 19 wherein each one of said first plurality of selective elements overlies one sensor element and is operably configured to transmit light having one of said first set of wavelengths while blocking light having any other of said first and second sets of wavelengths; and each one of said second plurality of selective elements overlies one sensor element and is operably configured to transmit light having one of said second set of wavelengths while blocking light having any other of said first and second sets of wavelengths.

21. The apparatus of claim 19 wherein:

each one of said first plurality of selective elements overlies a plurality of sensor elements and is operably configured to transmit light having said first set of wavelengths; and each one of said second plurality of selective elements overlies a plurality of sensor elements and is operably configured to transmit light having said second set of wavelengths.

22. The apparatus of claim 19 wherein each of said first and second sets of wavelengths comprises red, green, and blue wavelengths.

23. The apparatus of claim 12 wherein said discriminator comprises a discriminator coating applied to a surface of a lens element disposed proximate to said aperture plane.

24. The apparatus of claim 12 wherein said discriminator is operable to vary a distance between a centroid of said first portion of the imaging path and a centroid of said second portion of the imaging path to cause said first and second perspective viewpoints to change location while forming said first and second images, said change in perspective viewpoint location providing a corresponding change in said representation of said three dimensional spatial attributes.

25. The apparatus of claim 12 wherein said discriminator comprises a first adjustable aperture disposed to limit light transmitted through said first portion of said discriminator and a second adjustable aperture disposed to limit light transmitted through said second portion of said discriminator.

* * * * *

UNITED STATES PATENT AND TRADEMARK OFFICE
CERTIFICATE OF CORRECTION

| | |
|---|---|
| PATENT NO. | : 9,442,362 B2 |
| APPLICATION NO. | : 13/382892 |
| DATED | : September 13, 2016 |
| INVENTOR(S) | : Thomas N. Mitchell et al. |

It is certified that error appears in the above-identified patent and that said Letters Patent is hereby corrected as shown below:

In the Specification

In Column 1, Line 12, delete "INFORMATION," and insert -- INFORMATION", --, therefor.

In Column 1, Line 13, delete "PCT/CA2010/000957," and insert -- PCT/CA2009/000957, --, therefor.

In Column 1, Line 15, delete "APARATUS" and insert -- APPARATUS --, therefor.

In Column 1, Line 19, delete "below.;" and insert -- below. --, therefor.

In Column 7, Line 58, delete "signal;" and insert -- signal --, therefor.

In Column 9, Lines 34-35, delete "of the of the" and insert -- of the --, therefor.

In Column 10, Line 65, delete "-45°." and insert -- -45°). --, therefor.

In Column 11, Line 1, delete "+45°." and insert -- +45°). --, therefor.

In Column 11, Line 5, delete "-45°" and insert -- -45°) --, therefor.

In Column 11, Line 8, delete "+45°." and insert -- +45°). --, therefor.

In Column 11, Lines 9-14, delete "The wave plates 218 and polarizers 220 are substantially the same size and each wave plate marked "R" overlies a polarizer marked as "-" and each wave plate marked "L" overlies a polarizer marked as "+". The wave plates 218 and polarizers 220 may be fabricated by conventional lithographic deposition or processes, for example." and insert the same on Column 11, Line 8, as a continuation of the same paragraph.

In Column 11, Lines 11-12, delete ""L"overlies" and insert -- "L" overlies --, therefor.

Signed and Sealed this
Second Day of May, 2017

Michelle K. Lee
*Director of the United States Patent and Trademark Office*

CERTIFICATE OF CORRECTION (continued)
U.S. Pat. No. 9,442,362 B2

In Column 11, Line 40, delete "-45°"" and insert -- -45°) --, therefor.

In Column 11, Line 51, delete "+45°"" and insert -- +45°) --, therefor.

In Column 14, Line 12, delete "nelements" and insert -- elements --, therefor.

In Column 14, Line 13, delete "elemets." and insert -- elements. --, therefor.

In Column 16, Line 24, delete "Steropsis" and insert -- Stereopsis --, therefor.

In Column 16, Line 32, delete "+45°," and insert -- +45°), --, therefor.

In Column 16, Line 34, delete "then" and insert -- than --, therefor.

In Column 17, Line 9, delete "steropsis" and insert -- stereopsis --, therefor.

In Column 17, Line 17, delete "used" and insert -- use --, therefor.